US007914999B2

(12) United States Patent
Grenier et al.

(10) Patent No.: US 7,914,999 B2
(45) Date of Patent: Mar. 29, 2011

(54) NON-DENATURING LYSIS REAGENT

(75) Inventors: Frank C. Grenier, Libertyville, IL (US); Ryan F. Workman, Waukegan, IL (US); Hina N. Syed, Gurnee, IL (US); Salman Ali, Hoffman Estates, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/618,495

(22) Filed: Dec. 29, 2006

(65) Prior Publication Data
US 2008/0160499 A1 Jul. 3, 2008

(51) Int. Cl.
*G01N 33/53* (2006.01)
(52) U.S. Cl. .................. 435/7.1; 435/86; 436/4
(58) Field of Classification Search ............... 435/7.1, 435/7.91
See application file for complete search history.

(56) References Cited

U.S. PATENT DOCUMENTS

| | | | |
|---|---|---|---|
| 4,652,517 A | 3/1987 | Scholl et al. | |
| 5,134,875 A | 8/1992 | Jensen et al. | |
| 5,135,875 A | 8/1992 | Meucci et al. | |
| 5,169,773 A | 12/1992 | Rosenthaler et al. | |
| 5,217,971 A * | 6/1993 | Takasugi et al. | 514/254.02 |
| 5,322,772 A | 6/1994 | Soldin | |
| 5,350,574 A | 9/1994 | Erlanger et al. | |
| 5,354,845 A | 10/1994 | Soldin | |
| 5,489,668 A | 2/1996 | Morrison et al. | |
| 5,498,597 A | 3/1996 | Burakoff et al. | |
| 5,525,523 A | 6/1996 | Soldin | |
| 5,650,228 A | 7/1997 | May | |
| 5,650,288 A | 7/1997 | MacFarlane et al. | |
| 5,698,448 A | 12/1997 | Soldin | |
| 5,750,413 A * | 5/1998 | Morrison et al. | 436/537 |
| 5,780,307 A | 7/1998 | Soldin | |
| 5,897,990 A | 4/1999 | Baumann et al. | |
| 5,955,108 A * | 9/1999 | Sutton et al. | 424/489 |
| 5,990,150 A | 11/1999 | Matsui et al. | |
| 6,054,303 A | 4/2000 | Davalian et al. | |
| 6,087,134 A * | 7/2000 | Saunders | 435/91.2 |
| 6,187,547 B1 | 2/2001 | Legay et al. | |
| 6,197,588 B1 | 3/2001 | Gray et al. | |
| 6,239,102 B1 * | 5/2001 | Tiemessen | 514/9 |
| 6,328,970 B1 | 12/2001 | Molnar-Kimber et al. | |
| 6,410,340 B1 | 6/2002 | Soldin | |
| 6,541,612 B2 | 4/2003 | Molnar-Kimber et al. | |
| 6,858,439 B1 * | 2/2005 | Xu et al. | 436/518 |
| 6,913,580 B2 | 7/2005 | Stone | |
| 6,998,246 B2 | 2/2006 | Schäffler et al. | |
| 7,189,582 B2 | 3/2007 | Chen et al. | |
| 2002/0002273 A1 | 1/2002 | Sedrani et al. | |
| 2002/0022717 A1 | 2/2002 | Sedrani et al. | |
| 2002/0151088 A1 | 10/2002 | Molnar-Kimber et al. | |
| 2003/0157556 A1 | 8/2003 | Maggiore et al. | |
| 2003/0235839 A1 * | 12/2003 | McKernan et al. | 435/6 |
| 2004/0062793 A1 * | 4/2004 | Dyke | 424/445 |
| 2004/0101429 A1 | 5/2004 | Ogawa | |
| 2004/0102429 A1 | 5/2004 | Modak et al. | |
| 2005/0033035 A1 | 2/2005 | Beisel et al. | |
| 2005/0055126 A1 | 3/2005 | Genma et al. | |
| 2005/0112778 A1 * | 5/2005 | Wang et al. | 436/501 |
| 2005/0164323 A1 | 7/2005 | Chaudhary et al. | |
| 2005/0272109 A1 | 12/2005 | Schäffler et al. | |
| 2006/0003390 A1 | 1/2006 | Schäffler et al. | |
| 2008/0020401 A1 | 1/2008 | Grenier et al. | |
| 2008/0176756 A1 | 7/2008 | Siegel et al. | |
| 2009/0325193 A1 | 12/2009 | Grenier et al. | |
| 2009/0325197 A1 | 12/2009 | Drengler et al. | |
| 2009/0325198 A1 | 12/2009 | Holets-Mccormack | |

FOREIGN PATENT DOCUMENTS

| | | |
|---|---|---|
| EP | 0440044 A1 | 8/1991 |
| EP | 0693132 B1 | 1/1996 |
| EP | 0753744 A2 | 1/1997 |
| EP | 0973805 A1 | 1/2000 |
| EP | 1244800 B1 | 10/2002 |
| EP | 2118657 A2 | 11/2009 |
| WO | WO9005008 A1 | 5/1990 |
| WO | WO 92/18527 A1 | 10/1992 |
| WO | WO 92/19745 A1 | 11/1992 |
| WO | WO 93/25533 A1 | 12/1993 |
| WO | WO 94/24304 A1 | 10/1994 |
| WO | WO 94/25022 A1 | 11/1994 |
| WO | WO 94/25072 A1 | 11/1994 |
| WO | WO 95/16691 A1 | 6/1995 |
| WO | WO 95/25812 A2 | 10/1995 |
| WO | WO 96/12018 A2 | 4/1996 |
| WO | WO 96/13273 A1 | 5/1996 |
| WO | WO 97/03654 A2 | 2/1997 |
| WO | WO 98/00696 | 1/1998 |
| WO | WO9800696 A1 | 1/1998 |
| WO | WO 98/45333 A1 | 10/1998 |
| WO | WO9853315 A1 | 11/1998 |
| WO | WO 01/34816 A1 | 5/2001 |
| WO | WO2008/082979 A2 | 7/2008 |
| WO | WO2008/082982 A | 7/2008 |
| WO | WO2008/082984 A2 | 7/2008 |
| WO | WO2008082974 A2 | 7/2008 |

OTHER PUBLICATIONS

International Search Report and Written Opinion dated Oct. 8, 2008 issued in PCT/US07/88070.
International Search Report and Written Opinion dated Aug. 25, 2008 issued in PCT/US07/88056.
International Search Report and Written Opinion dated Sep. 24, 2008 issued in PCT/US07/88087 (WO2008/082979A2).
International Search Report and Written Opinion dated Sep. 24, 2008 issued in PCT/US07/88109 (WO2008/082984A2).
Alak et al., (Jun. 1997) "Measurement of Tacrolimus (FK506) and Its Metabolites: A Review of Assay Development and Application in Therapeutic Drug Monitoring and Pharmacokinetic Studies", *Therapeutic Drug Monitoring,* 19(3):338-351.
Bose, Biplab et al., (2003) "Characterization and Molecular Modeling of a Highly Stable Anti-Hepatitis B Surface Antigen scFv", *Molecular Immunology,* 40:617-631.

(Continued)

*Primary Examiner* — Jacob Cheu
(74) *Attorney, Agent, or Firm* — Paul D. Yasger; Audrey L. Bartnicki; Weaver Austin Villeneuve & Sampson LLP

(57) ABSTRACT

The invention provides a lysis reagent and method for preparing a test sample for use in an assay, wherein the method yields a homogeneous lysis mixture suitable for use in automated pipetting systems without the need for a centrifugation step. The lysis reagent includes a glycol and an alcohol. Other aspects of the invention include related immunoassays and test kits.

37 Claims, No Drawings

OTHER PUBLICATIONS

Hatfield, R.M. et al., (1987) "Development of an Enzyme-Linked Immunosorbent Assay for the Detection of Humoral Antibody to *Pasteurella Anatipestifer*", *Avian Pathology*, 16:123-140.

Kricka et al., (1999) "Human Anti-Animal Antibody Interferences in Immunological Assays", *Clinical Chemistry*, 45(7):942-952.

Sinha, et al., (2002) "Electrostatics in Protein Binding and Function", *Current Protein and Peptide Science*, 3:601-614.

Sinha, et al., (2007) "Understanding antibody-antigen associations by molecular dynamics simulations: Detection of important intra- and inter-molecular salt bridges", *Cell Biochem Biophys*, 47:361-375.

Tamura et al., (Oct. 1987) "A Highly Sensitive Method to Assay FK-506 Levels in Plasma", at pp. 23-29, of "FK-506 A Potential Breakthrough in Immunosuppression", *A Transplantation Proceedings Reprint*, Supplement 6, vol. XIX.

Uwatoko, Shu et al., (1984) "Characterization of C1q-Binding IgG Complexes in Systemic Lupus Erythematosus", *Clinical Immunology and Immunopathology*, 30:104-116.

European Supplemental Search Report and Search Opinion dated Apr. 9, 2010 issued in EP07869487.4.

Simamora et al., "Solubilization of rapamycin." *International Journal of Pharmaceutics* (2001); 213(1-2):25-29.

Clarke W., et al., "Immunoassays for therapeutic drug monitoring and clinical toxicology," Drug monitoring and clinical chemistry, 2004, 5, 95-112.

Kronquist K. E., et al., "Mechanism of alteration of the functional fraction of lipoprotein lipase in rat heart," Life Sci., 1980, 27(13), 1153-1158.

Le Meur Y, et al., "CYP3A5*3 influences sirolimus oral clearance in de novo and stable renal transplant recipients," Clin Pharmacol Ther., 2006, 80(1), 51-60.

Lee J. W., et al., "Tacrolimus (FK506): validation of a sensitive enzyme-linked immunosorbent assay kit for and application to a clinical pharmacokinetic study," Ther Drug Monit., 1997, 19(2), 201-207.

PCT International Search Report for Application No. PCT/US07/88098, dated May 27, 2008, 1 page.

Simamora P, et al., "Solubilization of rapamycin," Int J Pharm., 2001, 213(1-2), 25-29.

Supplementary European Search Report of EP Patent Application No. EP07869487, dated Mar. 19, 2010, issued Apr. 9, 2010, 8 pages total.

Supplementary European Search Report of EP Patent Application No. EP07865858, dated Mar. 19, 2010, issued Apr. 1, 2010, 9 pages total.

Supplementary European Search Report of EP Patent Application No. EP07869508, dated Mar. 19, 2010, issued Apr. 13, 2010, 11 pages total.

Supplementary European Search Report of EP Patent Application No. EP07861291, dated Jan. 11, 2010, issued Jan. 21, 2010, 11 pages total.

PCT International Search Report and Written Opinion for Application No. PCT/US07/10076, mailed Jul. 11, 2008, 11 pages total.

PCT International Search Report and Written Opinion for Application No. PCT/US07/88056, mailed Aug. 25, 2008, 11 pages total.

PCT International Search Report and Written Opinion for Application No. PCT/US07/88070, mailed Oct. 8, 2008, 11 pages total.

PCT International Search Report and Written Opinion for Application No. PCT/US07/88087, mailed Sep. 24, 2008, 12 pages total.

PCT International Search Report and Written Opinion for Application No. PCT/US07/88098, mailed May 27, 2008, 7 pages total.

PCT International Search Report and Written Opinion for Application No. PCT/US07/88109, mailed Sep. 24, 2008, 15 pages total.

USPTO Office Action dated Aug. 21, 2009, cover sheet and pp. 1-10, Notice of references cited by Examiner, Information Disclosure Statement by Applicant and considered by Examiner in U.S. Appl. No. 11/490,624.

Wilson D., et al., "Multi-center evaluation of analytical performance of the microparticle enzyme immunoassay for sirolimus," Clin Biochem., 2006, 39(4), 378-386.

Supplementary European Search Report of EP Patent Application No. EP07869487, dated Mar. 19, 2010, 8 pages total.

Clarke W., et al., "Immunoassays for therapeutic drug monitoring and clinical toxicology," Drug monitoring and clinical chemistry, 2004, 5, 95-112.

Kronquist K. E., et al., "Mechanism of alteration of the functional fraction of lipoprotein lipase in rat heart," Life Sci., 1980, 27(13), 1153-1158.

* cited by examiner

NON-DENATURING LYSIS REAGENT

CROSS-REFERENCE TO RELATED APPLICATIONS

Not applicable.

FIELD OF THE INVENTION

This invention relates to a non-denaturing lysis reagent useful, for example, in diagnostic immunoassays to determine the concentration levels of an immunosuppressant drug in a test sample.

BACKGROUND OF THE INVENTION

Many analytes of clinical interest are taken up by cells or become complexed with one or more other components of the test sample. Accordingly, to obtain an accurate measurement of the amount of analyte present in the sample, it is preferable to treat the sample, and/or conduct the assay under conditions, such that the analyte is released from the cells or other component(s) for detection in the assay.

For example, immunosuppressant drugs such as tacrolimus, everolimus, temsorolimus and cyclosporine are effective for the treatment of organ or tissue rejection following transplant surgery, of graft versus host disease and of autoimmune diseases in humans. During immunosuppressant drug therapy, monitoring the blood concentration levels of the immunosuppressant is an important aspect of clinical care because insufficient drug levels lead to graft (organ or tissue) rejection and excessive levels lead to undesired side effects and toxicities. Blood levels of immunosuppressant are therefore measured so drug dosages can be adjusted to maintain the drug level at the appropriate concentration. Diagnostic assays for determination of immunosuppressant blood levels have thus found wide clinical use.

Initially, the immunosuppressant must be extracted and separated from the other components of the patient sample. The bulk of the immunosuppressant drug in the patient sample is present in a complex with various "carrier" molecules, such as binding proteins. Sirolimus, tacrolimus and cyclosporine are found predominately in the red blood cells of patient specimens and are associated with specific binding proteins, FKBP for sirolimus and tacrolimus, and cyclophilin for cyclosporine. To ensure an accurate measurement of the total drug concentration in the specimen, the drug bound to the binding proteins is preferably liberated prior to quantitation. This has been addressed by using detergents to lyse cells and/or organic solvents to denature the sample proteins.

Following its extraction from the binding proteins, the drug can be measured in a number of different ways, including by immunoassay or chromatography with absorbance or mass spectrophotometric detection. Immunoassays for immunosuppressant drugs are available in a variety of formats, but all use the binding of an antibody or binding protein (e.g. FKBP) to the immunosuppressant drug. A commonly used immunoassay is an assay which involves the binding of a first antibody to the immunosuppressant and the binding of labeled immunosuppressant (e.g. acridinium-sirolimus) to the remaining free antibody binding sites, followed by quantitation by detection of the label.

SUMMARY OF THE INVENTION

The invention provides a method for preparing a test sample for use in an assay, the method comprising contacting the test sample with a lysis reagent to form a lysis mixture. The lysis reagent includes a glycol selected from the group consisting of ethylene glycol, propylene glycol, and an analog thereof, and at least one alcohol having five or fewer carbons is included in the lysis reagent or added to the lysis mixture. The alcohol can, for example, be methanol, ethanol, and/or propanol. In particular embodiments, the test sample includes a human blood sample.

Advantages of the sample preparation method of the invention include that the sample can be prepared for analysis without a centrifugation step and/or without the use of a detergent.

In preferred embodiments, the alcohol is included in the lysis reagent. In variations of such embodiments, the ratio of glycol to alcohol is in the range of about 4:1 to about 1:4 or, preferably, about 4:1 to about 1:2. The test sample can be added to any such lysis reagent at a ratio in the range of about 2:1 to about 1:2.

Where the method is carried out to prior to an assay for an analyte that is bound to one or more binding proteins in the test sample, the method can additionally include contacting the test sample or the lysis mixture with an agent that releases the analyte from the binding protein(s). The releasing agent can, for example, be an agent that competes with the analyte for binding to the binding protein(s). In an exemplary embodiment, the analyte includes an immunosuppressant drug, and the agent includes a different, but structurally similar, immunosuppressant drug. Where the analyte includes a non-protein molecule, the agent can, for example, include a protease that degrades the binding protein(s).

Another aspect of the invention is a lysis reagent mixture, which includes a glycol selected from the group consisting of ethylene glycol, propylene glycol, and an analog thereof and at least one alcohol having five or fewer carbons. In exemplary embodiments, the ratio of glycol to alcohol is in the range of about 4:1 to about 1:4 or, preferably, about 4:1 to about 1:2. This glycol-alcohol mixture is typically added to a test sample, in exemplary embodiments, at a ratio in the range of about 2:1 to about 1:2. Accordingly, the term "lysis reagent mixture" also includes the mixture that results from the addition of the glycol-alcohol mixture to the test sample. The alcohol can, for example, be methanol, ethanol, and/or propanol. In particular embodiments, the test sample includes a human blood sample.

The invention also provides a method for assessing the presence or concentration of an analyte in a test sample. This method entails contacting the test sample with a lysis reagent to form a lysis mixture and assaying the lysis mixture for the analyte. The lysis reagent includes a glycol selected from the group consisting of ethylene glycol, propylene glycol, and an analog thereof, and at least one alcohol having five or fewer carbons is included in the lysis reagent or added to the lysis mixture. The alcohol can, for example, be methanol, ethanol, and/or propanol. In particular embodiments, the test sample includes a human blood sample.

In exemplary embodiments, the alcohol is included in the lysis reagent, and the ratio of glycol to alcohol is in the range of about 4:1 to about 1:4 or, preferably, about 4:1 to about 1:2. This glycol-alcohol mixture is typically added to a test sample, in exemplary embodiments, at a ratio in the range of about 2:1 to about 1:2.

Advantages of the sample preparation method of the invention include that the lysis mixture is a homogeneous mixture, suitable for automated pipetting, without the need for a centrifugation step and/or without the use of a detergent. However, the test sample or the lysis mixture can be contacted with a detergent, if desired.

The lysis mixture can, for example, be analyzed by immunoassay. In exemplary embodiments, the analyte detected includes an immunosuppressant drug, such as, for example, sirolimus, tacrolimus, everolimus, temsorolimus, zotarolimus, cyclosporine, or analogs of any of these compounds.

In particular embodiments, the assay detects an analyte that is bound to one or more binding proteins in the test sample. In such embodiments, the method can additionally include contacting the test sample or the lysis mixture with an agent that releases the analyte from the binding protein(s). The releasing agent can, for example, be an agent that competes with the analyte for binding to the binding protein(s). In an exemplary embodiment, the analyte includes an immunosuppressant drug, and the agent includes a different, but structurally similar, immunosuppressant drug. Where the analyte includes a non-protein molecule, the agent can, for example, include a protease that degrades the binding protein(s).

Another aspect of the invention is a test kit including: (a) at least one antibody or protein capable of binding specifically to at least one analyte; (b) a lysis reagent including a glycol selected from the group consisting of ethylene glycol, propylene glycol, and an analog thereof; and (c) at least one alcohol having five or fewer carbons. The alcohol can, for example, be methanol, ethanol, and/or propanol. In preferred embodiments, the lysis reagent and alcohol(s) are combined and packaged in a single container. In variations of such embodiments, the ratio of glycol to alcohol is in the range of about 4:1 to about 1:4, preferably about 4:1 to about 1:2. The test kit can, optionally, contain a control composition including the at least one analyte of (a) and/or a detergent.

In exemplary embodiments, the analyte detected includes an immunosuppressant drug, such as, for example, sirolimus, tacrolimus, everolimus, temsorolimus, zotarolimus, cyclosporine, or analogs of any of these compounds.

In particular embodiments, the test kit additionally includes an agent that releases the analyte from one or more binding proteins in the test sample. The releasing agent can, for example, be an agent that competes with the analyte for binding to the binding protein(s). In an exemplary embodiment, the analyte includes an immunosuppressant drug, and the agent includes a different, but structurally similar, immunosuppressant drug. Where the analyte includes a non-protein molecule, the agent can, for example, include a protease that degrades the binding protein(s).

An exemplary, preferred test kit according to the invention includes: (a) at least one antibody or protein capable of binding specifically to at least one immunosuppressant drug selected from the group consisting of sirolimus, tacrolimus, everolimus, temsorolimus, zotarolimus and cyclosporine; (b) a lysis reagent including propylene glycol and ethanol at a ratio in the range of about 4:1 to about 1:2; and (c) control composition including the at least one immunosuppressant drug of (a).

DETAILED DESCRIPTION

The invention relates to a non-denaturing lysis reagent that can be mixed with a test sample to produce a homogeneous lysis mixture. This approach is superior to previous extraction methods that rely on the use of detergents or denaturants.

The use of detergents can be problematic, in particular formats because the quantity of detergent needed to quickly lyse and fragment cells may cause foaming, which is unacceptable for samples that must be pipetted by most automated pipetting systems, and may interfere with immunochemistry in samples to be analyzed immunoassay. The lysis reagent of the invention produces a sample that is not susceptible to foaming and eliminates the need for detergents, thus avoiding detergent driven interferences in assay immunochemistry.

The use of denaturants requires subsequent centrifugation steps to remove precipitated blood constituents, which reduces the efficiency of this approach. Additionally, the use of organic solvents at the concentration required can lead to sample evaporation that is significant enough to affect analyte concentration. The lysis reagent of the invention produces a homogeneous mixture that is suitable for use in automated pipetting systems without the need for a centrifugation step and eliminates the use of substantial concentrations of volatile organic solvents.

Definitions

Terms used in the claims and specification are defined as set forth below unless otherwise specified.

An "immunosuppressant drug" or "immunosuppressant", as used herein, refers to a therapeutic compound, either small molecule or antibody based, that has the same or similar chemical structure to either rapamycin (sirolimus) or cyclosporine, also known as cyclosporine A. Any known or hereafter developed analog of either rapamycin or cyclosporine is considered an immunosuppressant herein. Preferred immunosuppressants include sirolimus, tacrolimus, everolimus, temsorolimus, zotarolimus and cyclosporine. Tacrolimus and cyclosporine are calcineurin inhibitors that suppress early activation of the immune system's T lymphocytes through inhibition of cytokines such as interleukin 2. In contrast, the primary target of sirolimus, everolimus and zotarolimus is mammalian target of rapamycin (mTOR), a specific cell-cycle regulatory protein. The inhibition of mTOR leads to suppression of cytokine-driven T-lymphocyte proliferation.

The chemical formula of cyclosporine is in Formula A. The chemical formula of sirolimus (rapamycin) is in Formula B. The chemical formula of the structural difference of everolimus (RAD) from sirolimus is in Formula C.

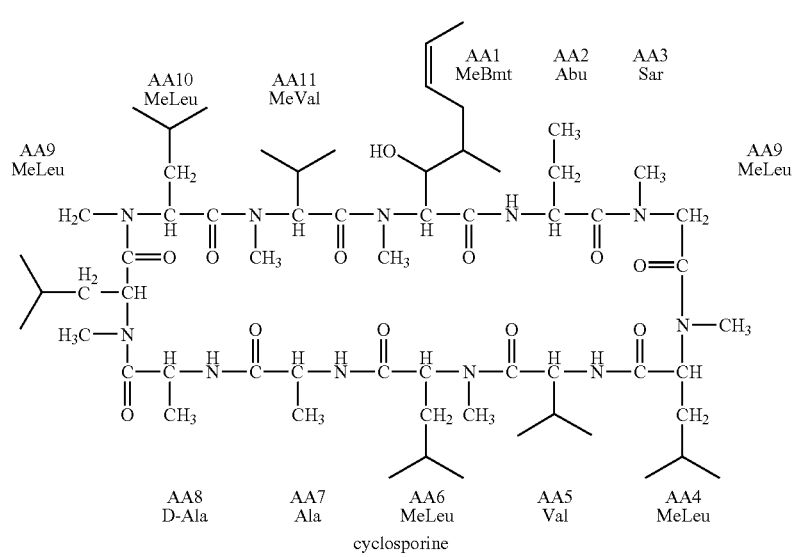

cyclosporine

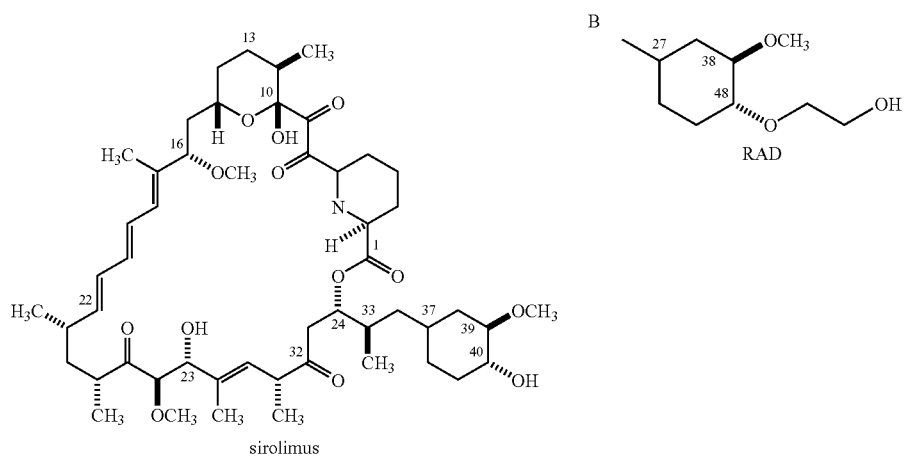

sirolimus          RAD

Numerous derivatives or analogs of cyclosporine have been prepared. The invention comprises lysis reagents, lysis methods, assays and assay kits for cyclosporine or any of its analogs.

Numerous derivatives or analogs of rapamycin have been prepared. For example, these include the preparation of ester mono- and di-ester derivatives of rapamycin (WO 92/05179), 27-oximes of rapamycin (EP0 467606); 42-oxo analog of rapamycin (U.S. Pat. No. 5,023,262); bicyclic rapamycins (U.S. Pat. No. 5,120,725); rapamycin dimers (U.S. Pat. No. 5,120,727); silyl ethers of rapamycin (U.S. Pat. No. 5,120, 842); and arylsulfonates and sulfamates (U.S. Pat. No. 5,177, 203). Rapamycin was recently synthesized in its naturally occurring enantiomeric form (K. C. Nicolaou et al., *J. Am. Chem. Soc.*, 1993, 115, 4419-4420; S. L. Schreiber, *J. Am. Chem. Soc.*, 1993, 115, 7906-7907; S. J. Danishefsky, *J. Am. Chem. Soc.*, 1993, 115, 9345-9346. The invention comprises lysis reagents, lysis methods, assays and assay kits for rapamycin or any of its analogs.

Another immunosuppressant analog of rapamycin is FK-506, also known as tacrolimus, which was isolated from a strain of *S. tsukubaensis*. FK-506's chemical formula is published in European Patent EP 0 293 892 B1. Analogs of FK-506 include the related natural products FR-900520 and FR-900523, which differ from FK-506 in their alkyl substituent at C-21, and were isolated from *S. hygroscopicus yakushimnaensis*. Another analog, FR-900525, produced by *S. tsukubaensis*, differs from FK-506 in the replacement of a pipecolic acid moiety with a proline group. The invention comprises lysis reagents, lysis methods, assays and assay kits for FK-506 or any of its analogs. Temsorolimus is another ester derivative of sirolimus which can be monitored with the invention.

ABT-578 [40-epi-(1-tetrazolyl)-rapamycin], known better today as zotarolimus, is a semi-synthetic macrolide triene antibiotic derived from rapamycin. Zotarolimus structure is shown in Formula D.

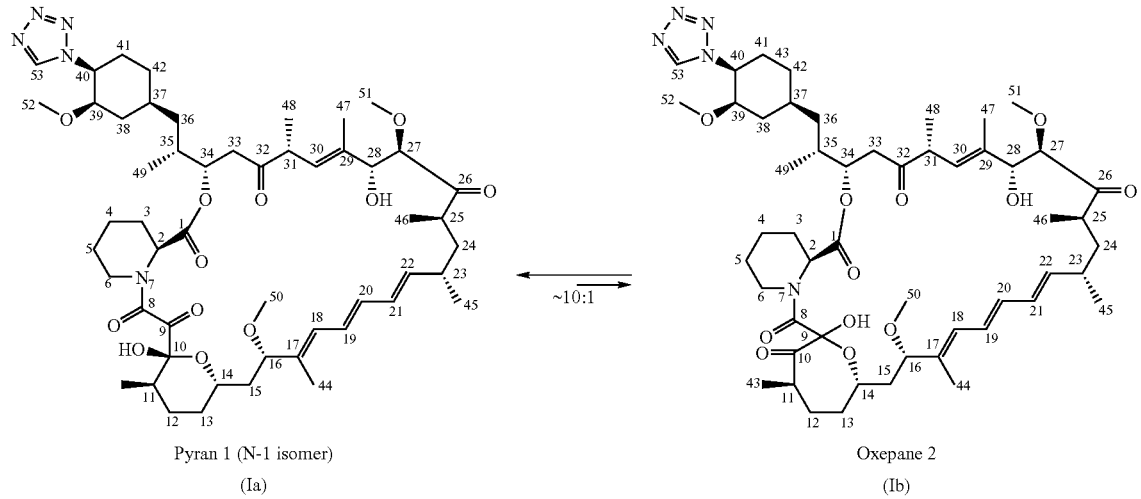

Formula D
The isomers of zotarolimus

Pyran 1 (N-1 isomer)
(Ia)

Oxepane 2
(Ib)

As used herein with reference to an immunosuppressant drugs, the term "structurally similar" indicates that the drugs have sufficiently similar structures that the drugs bind competitively to at least one common binding partner (e.g., a binding protein).

The term "test sample" refers to a component, tissue or fluid of an animal's body that is the source of the immunosuppressant drug analyte. These components, tissues and fluids include human and animal body fluids such as whole blood, serum, plasma, synovial fluid, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens. Preferably, the test sample is a human peripheral blood sample.

As used herein, an "antibody" refers to a protein consisting of one or more polypeptides substantially encoded by immunoglobulin genes or fragments of immunoglobulin genes. This term encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

Thus, the term "antibody," as used herein, also includes antibody fragments either produced by the modification of whole antibodies or synthesized de novo using recombinant DNA methodologies. The term "antibody" also encompasses single chain antibodies (antibodies that exist as a single polypeptide chain), more preferably single chain Fv antibodies (sFv or scFv), in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated, light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

"Analyte," as used herein, refers to the substance to be detected, which may be present in the test sample. The analyte can be any substance for which there exists a naturally occurring specific binding partner or for which a specific binding partner can be prepared. Thus, an analyte is a substance that can bind to one or more specific binding partners in an assay.

A "binding partner," as used herein, is a member of a binding pair, i.e., a pair of molecules wherein one of the molecules binds to the second molecule. Binding partners that bind specifically are termed "specific binding partners." In addition to the antigen and antibody binding partners commonly used in immunoassays, other specific binding partners can include biotin and avidin, carbohydrates and lectins, complementary nucleotide sequences, effector and receptor molecules, cofactors and enzymes, enzyme inhibitors and enzymes, and the like. Immunoreactive specific binding partners include antigens, antigen fragments, antibodies and antibody fragments, both monoclonal and polyclonal, and complexes thereof, including those formed by recombinant DNA methods.

The term "specific binding" is defined herein as the preferential binding of binding partners to another (e.g., a polypeptide and a ligand (analyte), two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

An antibody that specifically binds an immunosuppressant drug is said to be "specific for" that immunosuppressant drug.

The term "capture agent" is used herein to refer to a binding partner that binds to analyte, preferably specifically. Capture agents can be attached to a solid phase. As used herein, the binding of a solid phase-affixed capture agent to analyte forms a "solid phase-affixed complex."

The term "labeled detection agent" is used herein to refer to a binding partner that binds to analyte, preferably specifically, and is labeled with a detectable label or becomes labeled with a detectable label during use in an assay.

A "detectable label" includes a moiety that is detectable or that can be rendered detectable.

As used with reference to a labeled detection agent, a "direct label" is a detectable label that is attached, by any means, to the detection agent.

As used with reference to a labeled detection agent, an "indirect label" is a detectable label that specifically binds the detection agent. Thus, an indirect label includes a moiety that is the specific binding partner of a moiety of the detection agent. Biotin and avidin are examples of such moieties that are employed, for example, by contacting a biotinylated antibody with labeled avidin to produce an indirectly labeled antibody.

As used herein, the term "indicator reagent" refers to any agent that is contacted with a label to produce a detectable signal. Thus, for example, in conventional enzyme labelling, an antibody labeled with an enzyme can be contacted with a substrate (the indicator reagent) to produce a detectable signal, such as a colored reaction product.

As used herein, a "glycol analog" is any glycol having from two to six carbon atoms.

A lysis mixture is said to be "homogeneous" when it is sufficiently free of large particulates to allow accurate and reliable pipetting (either manually or using an automated system).

I. Sample Collection and Processing

The methods of the invention are generally carried out on test samples derived from an animal, preferably a mammal, and more preferably a human.

The methods of the invention can be carried out using any sample that may contain the analyte of interest (e.g., an immunosuppressant drug), such as a blood sample.

The sample is collected by any standard technique and then contacted with a lysis reagent to form a lysis mixture. The lysis reagent includes a glycol having from two to six carbon atoms. At least one alcohol having five or fewer carbons is included in the lysis reagent or added to the lysis mixture. In preferred embodiments, the lysis reagent includes the alcohol(s). Glycols suitable for use in the lysis reagent include, for example, ethylene glycol, propylene glycol, and analogs thereof, as well as mixtures of such glycols. Alcohols suitable for use in the invention include, for example, methanol, ethanol, propanol, and mixtures thereof. In particular embodiments, the ratio of glycol to alcohol is in the range of about 5:1 to about 1:5, 4:1 to about 1:4, 2:1 to about 1:2, or about 1:1 (volume:volume). In more particular embodiments, the ratio of glycol to alcohol is in the range of about 4:1 to about 1:2.

The lysis mixture can formed by any mixing technique at any desirable temperature to contact any chosen amount of the sample with the lysis reagent. The sample is contacted with a sufficient volume of lysis reagent to lyse the cells in the sample and produce a homogeneous mixture. For a lysis reagent wherein the ratio of glycol to alcohol is in the range of about 4:1 to about 1:4, as described above, sample can be added to the lysis reagent at a ratio in the range of about 2:1 to about 1:2, about 1:3, about 1:4, about 1:5, or about 1:10; e.g., about 1:1 (volume:volume), or any other range including these values as endpoints, depending on the lysis reagent composition. For example, about 100 uL to about 600 uL of blood sample can be mixed with about 50 uL to about 1200 uL of the lysis reagent for up to about five minutes. In certain embodiments, the lysis mixture is formed by mixing 150 uL of blood sample with 300 uL of lysis reagent and vortexing vigorously for 5-10 seconds. In preferred embodiments, lysis is complete in less than a minute at room temperature. The lysis mixture is then assayed for the analyte using a suitable assay. In preferred embodiments, the lysis mixture is produced, ready for analysis, without the need to centrifuge the sample.

The lysis reagent of the invention can be employed without any added detergent. However, in certain embodiments, one or more detergents can be added, if desired. Detergents typically do not foam in the presence of the lysis reagent, and thus lysis mixtures prepared according to the invention are amenable to automated pipetting, regardless of whether a detergent is included. If included in a lysis mixture intended for immunoassay, the detergent is preferably present at a concentration that does not interfere with the immunochemistry. Preferably, the detergent is a non-ionic detergent, such as saponin, and is employed at a concentration in the range of about 0.01% to 0.1%, more preferably about 0.1%. U.S. Pat. No. 5,650,288 (issued Jul. 22, 1997 to MacFarlane and Jensen; hereby incorporated by reference in its entirety) describes the use of detergents and in immunoassays for immunosuppressants.

In particular embodiments, where the analyte is bound to one or more binding proteins in the test sample, the method can additionally entail contacting the test sample with an agent that releases the analyte from the binding protein(s). This agent can be included in the lysis reagent, if desired. The agent can, for example, be one that competes with the analyte for binding to the binding protein(s). The agent is generally selected so that it will not affect the results of the assay to be carried out. Thus, for instance, if the assay is an immunoassay, the agent is typically one that the relevant antibody does not cross-react with. Where the analyte is an immunosuppressant drug, the agent can be a different, but structurally similar, immunosuppressant drug. For example, sirolimus and tacrolimus both bind FKBP, and, for this reason, sirolimus can be used to release tacrolimus from FKBP and vice versa. Any subsequent immunoassay will generally employ an antibody that distinguishes between sirolimus and tacrolimus. U.S. Pat. No. 6,187,547 (issued Feb. 13, 2001 to Legay and Wenger; incorporated herein by reference in its entirety) describes "binding competitors" useful for releasing immunosuppressant drugs from binding proteins. Examples include: [$Thr^2$, $Leu^5$, $D-Hiv^8$, $Leu^{10}$]-Ciclosporin, which can release cyclosporine.

Where the analyte is a non-protein molecule, a protease can be employed to release the analyte from binding protein(s). The protease used in the method should be one that can degrade the binding protein, thereby releasing the analyte for assay and can be inactivated without adversely affecting the sensitivity and the precision of the assay to be carried out. Care should be taken in obtaining enzymes free from other contaminating enzymes that might not be inactivated by the method of inactivation used. Otherwise, any residual proteolytic activity could degrade an antibody used in a subsequent immunoassay. Exemplary proteases include proteinase K, subtilisin, dispase, thermolysin, trypsin, ficin, bromelain, and combinations thereof.

Proteinase K (Sigma Chemical Co., St. Louis, Mo.) is a nonspecific, Ca-dependent protease that can be inactivated by heat (65° C. or higher) and by specific protease inhibitors, such as phenyl methyl sulfonyl fluoride (PMSF, Boehringer Mannheim, Indianapolis, Ind.) or diisopropylfluorophosphate (DFP, Calbiochem, La Jolla, Calif.). Subtilisin (Sigma) is also a nonspecific, Ca-dependent protease that can be inactivated by heat (55° C. or higher), although it can be inhibited by acidic pH or a specific protease inhibitor, such as PMSF, DFP or aprotinin.

Dispase (Boehringer Mannheim or Sigma or Calbiochem) and thermolysin (Sigma or Boehringer Mannheim) are Ca-dependent metallo-proteases, which can be inactivated by EDTA, at a concentration of about 5 mM, for example. When dispase and thermolysin combined are used as the protease, proteolysis is preferably inactivated by addition of a divalent cation chelator, such as EDTA, at a concentration of about 5 mM, for example, in the presence of a zinc salt, e.g., $ZnSO_4$, at a concentration of about 40 mM, for example.

Trypsin (Worthingtom Enzymes, Freehold, N.J.) cleaves proteins specifically at the carboxyl side of lysine or arginine residues and can be inhibited by heat (90° C. or higher) or specifically inhibited by many agents, including aprotinin (Trasylol, Miles, Kankakee, Ill. or Calbiochem), leupeptin (Sigma or Boehringer Mannheim), PMSF, or specific trypsin inhibitors derived from soybean, lima bean or egg white (Worthington or Sigma). Ficin is a thiol protease that can be inactivated by $HgCl_2$, at a concentration of about 2 mM, for example. Bromelain is also a thiol protease and can be inactivated by bromelain inhibitor (Sigma).

In particular embodiments, the concentration of protease is high enough to degrade to the binding proteins within about 30 min, preferably within about 20 min, yet low enough to allow efficient inactivation of the enzyme. Accordingly, the concentration of protease is preferably be in the range of about 0.5 to 2.0 units/ml, more preferably about 1 unit/ml.

After lysis and release from binding proteins, if applicable, the analyte can be measured using any standard technique for detecting that analyte, e.g., immunoassay or chromatography with absorbance or mass spectrophotometric detection. For detection of immunosuppressant drugs, immunoassays are conveniently employed.

II. Immunoassays

A. In General

Immunoassays according to the invention can be used for the qualitative identification and/or the quantification of analyte in a test sample. These methods are applicable, for example, to immunoassays of immunosuppressant drugs, such as rapamycin (sirolimus), tacrolimus, everolimus, temsorolimus, zotarolimus, cyclosporine, and analogs of any of these compounds. Such immunoassays can be carried out by combining a lysis reagent with the test sample to form a lysis mixture, as described above. The lysis mixture can be contacted with at least one antibody specific for the analyte under conditions suitable for binding of the antibody to the analyte, if present, to form an assay mixture, and binding of the antibody to the analyte is then detected.

In certain embodiments, enhanced assay sensitivity can be achieved by contacting the lysis mixture with the antibody in the presence of a salt concentration of greater than about 0.4 M. In particular embodiments, the salt concentration is less than or equal to about 4.0 M. In exemplary embodiments, the salt concentration is about 2.0 M. Suitable salts can include, for example, any of the following anions: fluoride, chloride, bromide, iodide, thiocyanate, acetate, citrate, and bisulfate. In particular embodiments, the salt includes a monovalent anion, such as, for example: fluoride, chloride, bromide, iodide, thiocyanate, and acetate. In preferred embodiments, the salt includes chloride, e.g., a chloride salt of an alkali metal (e.g., lithium, sodium, potassium, rubidium, cesium). Generally, the salt employed is soluble under the assay conditions. Sodium chloride is highly soluble under most conditions, and can thus be conveniently used to enhance assay sensitivity in a wide variety of immunoassays according to the invention.

The salt can be provided to the assay mixture in any convenient manner and can be present before, or added after, contact between the lysis mixture and the antibody. In particular embodiments, the salt is provided in an assay diluent, which can also optionally include one or more other components, in addition to water (such as, for example, a buffer). The salt concentration in the assay diluent will vary, depending on the desired final salt concentration and on the amount of diluent added to the assay mixture. For example, an assay diluent having a salt concentration of about 4.0 M could be added to an equal volume of assay mixture to provide a final salt concentration of 2.0 M.

B. Antibodies

In immunoassays for the qualitative or quantitative detection of an analyte in a test sample, at least one antibody that binds to the analyte is contacted with a lysis mixture suspected of containing the analyte to form an antibody-analyte immune complex. To detect immunosuppressant drugs, any suitable antibodies that bind to the particular drug can be used in immunoassay according to the invention. Antibodies to each of rapamycin (sirolimus), tacrolimus, zotarolimus, cyclosporine and everolimus are known in the art, and any of these can be used. It is preferred to use the monoclonal antibody that is a component of Abbott Laboratories' commercially available IM Sirolimus assay for measuring sirolimus.

An exemplary protocol for producing an antibody specific for an immunosuppressant drug is as follows. Female RBf/Dnj mice are administered 3 monthly boosts of a drug-27-CMO-tetanus toxoid immunogen followed by an immunization with drug-42-HS-tetanus toxoid preparation on the 4th month. Seven months later, an intrasplenic pre-fusion boost is administered to the animal using the drug-27-CMO-tetanus toxoid immunogen 3 days prior to the fusion. Splenic B-cells are then isolated and used in a standard polyethylene (PEG)

fusion with the SP2/0 myeloma. Confluent cultures are screened for anti-drug activity 10-14 days later in a microtiter EIA and positive cultures are then cloned using limiting dilution technique. The resulting clones are isolated and scaled up in IMDM w/FBS (Invitrogen) tissue culture medium and the secreted antibody is affinity purified using Protein A. An exemplary, preferred antibody generated using sirolimus as the drug can be used in immunoassays for sirolimus, everolimus and zotarolimus.

An exemplary, preferred antibody for use in immunoassays for tacrolimus is described in M. Kobayashi et al., "A Highly Sensitive Method to Assay FK-506 Levels in Plasma", at pp 23-29 of "FK-506 A Potential Breakthrough in Immunosuppression", *A Transplantation Proceedings Reprint*, Supplement 6, Vol. XIX, October, 1987, Editors T. Starzl, L. Makowka and S. Todo, published by Grune & Stratton, Inc., Philadelphia, Pa.

An exemplary, preferred antibody for use in immunoassays for cyclosporine is the monoclonal antibody that is a component of Abbott Laboratories' commercially available AxSYM cyclosporine assay for measuring cyclosporine.

C. Detection

The antibody-analyte immune complexes can then detected using any suitable technique. For example, an antibody can be labeled with a detectable label to detect the presence of the antibody-analyte complex. The selection of a particular label is not critical, but the chosen label must be capable of producing a detectable signal either by itself or in conjunction with one or more additional substances.

Useful detectable labels, their attachment to antibodies and detection techniques therefor are known in the art. Any detectable label known in the art can be used. For example, the detectable label can be a radioactive label, such as, $^{3}H$, $^{125}I$, $^{35}S$, $^{14}C$, $^{32}P$, $^{33}P$; an enzymatic label, such as horseradish peroxidase, alkaline peroxidase, glucose 6-phosphate dehydrogenase, etc.; a chemiluminescent label, such as, acridinium derivatives, luminol, isoluminol, thioesters, sulfonamides, phenanthridinium esters, etc.; a fluorescent label, such as, fluorescein (5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemi* (1996), which is a combined handbook and catalogue published by Molecular Probes, Inc., Eugene, Oreg., each of which is incorporated herein by reference. Preferred labels for use with the invention are chemiluminescent labels such as acridinium-9-carboxamide. Additional detail can be found in Mattingly, P. G., and Adamczyk, M. (2002) Chemiluminescent N-sulfonylacridinium-9-carboxamides and their application in clinical assays, in *Luminescence Biotechnology: Instruments and Applications* (Dyke, K. V., Ed.) pp 77-105, CRC Press, Boca Raton.

The detectable label can be bound to the analyte, analyte analog, or antibody either directly or through a coupling agent. An example of a coupling agent that can be used is EDAC (1-ethyl-3-(3-dimethylaminopropyl)carbodiimide, hydrochloride), which is commercially available from Sigma-Aldrich (St. Louis, Mo.). Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

Alternatively, a second antibody that binds to analyte and that contains a detectable label can be added to the lysis mixture and used to detect the presence of the antibody-analyte complex. Any suitable detectable label can be used in this embodiment.

D. Exemplary Formats

The immunoassays of the invention can be conducted using any format known in the art, such as, but not limited to, a sandwich format, a competitive inhibition format (including both forward or reverse competitive inhibition assays) or a fluorescence polarization format. The exemplary formats described below are described in terms of assaying an immunosuppressant drug. However, as those of skill in the art appreciate, the described formats are applicable to any analyte.

In immunoassays for the quantitative detection of an immunosuppressant, such as a preferred sandwich type format, at least two antibodies are employed to separate and quantify the drug in the lysis mixture. More specifically, the at least two antibodies bind to different parts of the drug, forming an immune complex which is referred to as a "sandwich". Generally, one or more antibodies can be used to capture the immunosuppressant in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, it is preferred that both antibodies binding to the drug are not diminished by the binding of any other antibody in the assay to its respective binding site. In other words, antibodies should be selected so that the one or more first antibodies brought into contact with a lysis mixture suspected of containing an immunosuppressant do not bind to all or part of the binding site recognized by the second or subsequent antibodies, thereby interfering with the ability of the one or more second or subsequent antibodies to bind to the drug. In a sandwich assay, the antibodies, and preferably, the at least one capture antibody, are used in molar excess amounts relative to the maximum amount of drug expected in the lysis mixture. For example, from about 5 µg/mL to about 1 mg/mL of antibody per mL of solid phase containing solution can be used.

In one embodiment, the at least one first capture antibody can be bound to a solid support which facilitates the separation of the first antibody-drug complex from the test sample. The solid support or "solid phase" used in the inventive immunoassay is not critical and can be selected by one skilled in the art. A solid phase or solid support, as used herein, refers to any material that is insoluble, or can be made insoluble by a subsequent reaction. Useful solid phases or solid supports are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (a registered trademark of Abbott Laboratories, Abbott Park, Ill.), which are red blood cells "fixed" by pyruvic aldehyde and formaldehyde, and others. Suitable methods for immobilizing peptides on solid phases include ionic, hydrophobic, covalent interactions and the like. The solid phase can be chosen for its intrinsic ability to attract and immobilize the capture agent. Alternatively, the solid phase can comprise an additional receptor which has the ability to attract and immobilize the capture agent. The additional receptor can include a charged substance that is oppositely charged with respect to the capture agent itself or to a charged substance conjugated to the capture agent. As yet another alternative, the receptor can be any specific binding partner which is immobilized upon (attached to) the solid phase and which has the ability to immobilize the capture agent through a specific binding reaction. The receptor molecule enables the indirect binding of the capture agent to a solid phase material before the performance of the assay or during the performance of the assay.

Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind the drug. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

It is within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by hydrophobic forces.

After the lysis mixture suspected of containing or containing the immunosuppressant is brought into contact with the at least one first capture antibody, the resulting assay mixture is incubated to allow for the formation of a first capture antibody (or multiple antibody)-drug complex. The incubation can be carried out at any suitable pH, including a pH of from about 4.5 to about 10.0, at any suitable temperature, including from about 2° C. to about 45° C., and for a suitable time period from at least about one (1) minute to about eighteen (18) hours, preferably from about 4-20 minutes, most preferably from about 17-19 minutes.

After the addition of a detection agent and the formation of a labeled complex, the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of drug in the test sample can be determined by use of a standard curve that has been generated, for example, using serial dilutions of immunosuppressant drug of known concentration. Other than using serial dilutions of the drug, the standard curve can be generated gravimetrically, by mass spectroscopy and by other techniques known in the art.

In a preferred forward competitive format, an aliquot of labeled drug, or analogue thereof, of a known concentration is used to compete with the drug present in a test sample for binding to the antibody. In a forward competition assay, an immobilized antibody can either be sequentially or simultaneously contacted with the test sample and a labeled drug or drug analogue thereof. The drug or drug analogue can be labeled with any suitable detectable label, including those detectable labels discussed above. In this assay, the capture antibody can be immobilized on to a solid support using the techniques discussed previously herein. Alternatively, the capture antibody can be coupled to an antibody, such as an antispecies antibody, that has been immobilized on to a solid support, such as a microparticle.

The labeled drug or drug analogue, the lysis mixture and the antibody are incubated under conditions similar to those described above in connection with the sandwich assay format. Two different types of antibody-drug complexes are then generated. Specifically, one of the antibody-drug complexes generated contains a detectable label while the other antibody-drug complex does not contain a detectable label. The antibody-drug complex can be, but does not have to be, separated from the remainder of the assay mixture prior to quantification of the detectable label. Regardless of whether the antibody-drug complex is separated from the remainder of the assay mixture, the amount of detectable label in the antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

The antibody-drug complex can be separated from the assay mixture by binding the antibody to a solid support, such as the solid supports discussed above in connection with the sandwich assay format, and then removing the remainder of the assay mixture from contact with the solid support.

In a reverse competition assay, an immobilized immunosuppressant drug or analogue thereof can either be sequentially or simultaneously contacted with a lysis mixture and at least one labeled antibody. The antibody can be labeled with any suitable detectable label, including those detectable labels discussed above. The drug or drug analogue can be bound to a solid support, such as the solid supports discussed above in connection with the sandwich assay format.

The immobilized drug or drug analogue, lysis mixture, and at least one labeled antibody are incubated under conditions similar to those described above in connection with the sandwich assay format. Two different types of antibody-drug complexes are then generated. Specifically, one of the antibody-drug complexes generated is immobilized and contains a detectable label while the other antibody-drug complex is not immobilized and contains a detectable label. The non-immobilized antibody-drug complex and the remainder of the assay mixture are removed from the presence of the immobilized antibody-drug complex through techniques known in the art, such as washing. Once the non-immobilized antibody-drug complex is removed, the amount of detectable label in the immobilized antibody-drug complex is then quantified. The concentration of drug in the test sample can then be determined by comparing the quantity of detectable label in the antibody-drug complex to a standard curve. The standard curve can be generated using serial dilutions of the drug of known concentration, by mass spectroscopy, gravimetrically and by other techniques known in the art.

In a fluorescence polarization assay, in one embodiment, an antibody or functionally active fragment thereof is first contacted with an unlabeled lysis mixture containing the immunosuppressant drug to form an unlabeled antibody-drug complex. The unlabeled antibody-drug complex is then contacted with a fluorescently labeled drug or analogue thereof. The labeled drug or drug analogue competes with any unlabeled drug in the assay mixture for binding to the antibody or functionally active fragment thereof. The amount of labeled antibody-drug complex formed is determined and the amount of drug in the test sample determined via use of a standard curve.

The use of scanning probe microscopy (SPM) for immunoassays also is a technology to which the immunoassay methods of the present invention are easily adaptable. In SPM, in particular in atomic force microscopy, a capture agent is affixed to a solid phase having a surface suitable for scanning. The capture agent can, for example, be adsorbed to a plastic or metal surface. Alternatively, the capture agent can be covalently attached to, e.g., derivatized plastic, metal, silicon, or glass according to methods known to those of ordinary skill in the art. Following attachment of the capture agent, the lysis mixture is contacted with the solid phase, and a scanning probe microscope is used to detect and quantify solid phase-affixed complexes. The use of SPM eliminates the need for labels which are typically employed in immunoassay systems. Such a system is described in U.S. application Ser. No. 662,147, which is incorporated herein by reference.

Immunoassays according to the invention can also be carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the invention is the Protiveris' multicantilever array. This array is based on chemo-mechanical actuation of specially designed silicon microcantilevers and subsequent optical detection of the microcantilever deflections. When coated on one side with a binding partner, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

In other embodiments, immunoassays according to the invention are carried out using electrochemical detection. A basic procedure for electrochemical detection has been described by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 . mu.l to 360 µL have been reported previously. In capillary immunoassays with electrochemical detection, the lowest detection limit reported thus far is 3000 molecules of mouse IgG using a volume of 70 µL and a 30 min or 25 min assay time.

Various electrochemical detection systems are described in U.S. Pat. No. 7,045,364 (issued May 16, 2006; incorporated herein by reference), U.S. Pat. No. 7,045,310 (issued May 16, 2006; incorporated herein by reference), U.S. Pat. No. 6,887,714 (issued May 3, 2005; incorporated herein by reference), U.S. Pat. No. 6,682,648 (issued Jan. 27, 2004; incorporated herein by reference); U.S. Pat. No. 6,670,115 (issued Dec. 30, 2003; incorporated herein by reference).

In particular embodiments, useful, for example, for simultaneously assaying multiple analytes in one test sample, the solid phase can include a plurality different capture agents. Thus, for example, the solid phase can have affixed thereon a plurality of antibodies, wherein each is intended to test for the presence of different analytes in the sample. In an exemplary embodiment, the solid phase can consist of a plurality of different regions on a surface, wherein each region has a particular antibody affixed therein.

Multiplex formats can, but need not, employ a plurality of labels, wherein each label is used for the detection of a particular analyte. For example, multiple, different analytes can be detected without using a plurality of labels where a plurality of capture agents, such as antibodies, are affixed to the solid phase at different known locations, based on specificity. Because the specificity of the capture agent at each location is known, the detection of a signal at a particular location can be associated with the presence of analyte bound at that location. Examples of this format include microfluidic devices and capillary arrays, containing different capture agents at different locations along a channel or capillary, respectively, and microarrays, which typically contain different capture agents arranged in a matrix of spots ("target elements") on a surface of a solid support. In particular embodiments, each different capture agent can be affixed to a different electrode, which can, for example, be formed on a surface of a solid support, in a channel of a microfluidic device, or in a capillary.

III. Test Kits

The invention also provides test kits for assaying test samples for an analyte. Test kits according to the invention include one or more reagents useful for practicing one or more immunoassays according to the invention. A test kit generally includes a package with one or more containers holding the reagents, as one or more separate compositions or, optionally, as admixture where the compatibility of the reagents will allow. The test kit can also include other material(s), which may be desirable from a user standpoint, such as a buffer(s), a diluent(s), a standard(s), and/or any other material useful in sample processing, washing, or conducting any other step of the assay.

In particular embodiments, test kits of the invention can include: (a) at least one antibody or protein capable of binding specifically to at least one analyte; and (b) a lysis reagent comprising: a glycol selected from the group consisting of ethylene glycol, propylene glycol, and an analog thereof; and at least one alcohol having five or fewer carbons. In exemplary embodiments, useful for carrying out immunoassays for immunosuppressant drugs, the antibody can be specific for rapamycin (sirolimus), tacrolimus, everolimus, temsorolimus, zotarolimus, cyclosporine, or analogs of any of these compounds.

In certain embodiments, the lysis reagent includes methanol, ethanol, propanol, or a mixture of any of these alcohols. In exemplary embodiments, the ratio of glycol to alcohol is in the range of about 4:1 to about 1:4, more particularly, in the range of about 4:1 to about 1:2.

If desired, the test kit can additionally include a control composition that includes the analyte being assayed.

In particular embodiments, test kits according to the invention can include one or more detergents and/or agents that release the analyte from one or more binding proteins in the test sample. Suitable detergents or detergent combinations include non-ionic detergents, such as saponin, as described above. Suitable releasing agents include agents that compete with the analyte for binding to one or more binding proteins, as described above, and proteases, which can be used to degrade binding proteins and liberate non-protein analytes. Exemplary proteases include proteinase K, subtilisin, dispase, thermolysin, trypsin, ficin, bromelain, and combinations thereof. Any detergents or proteases provided in kits of the invention should be provided in a manner that facilitates the production of a lysis mixture containing the components in suitable concentration, as described above.

Kits according to the invention can include a solid phase and a capture agent that is affixed to the solid phase or that becomes solid phase-affixed during the assay. In exemplary embodiments, the solid phase includes one or more microparticles or electrodes. Where such kits are to be employed for conducting sandwich immunoassays, the kits can additionally include a labeled detection agent. In certain embodiments, the test kit includes at least one direct label, such as acridinium-9-carboxamide. Test kits according to the invention can also include at least one indirect label. If the label employed generally requires an indicator reagent to produce a detectable signal, the test kit preferably includes one or more suitable indicator reagents.

Test kits according to the invention preferably include instructions for carrying out one or more of the immunoassays of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, the commonly owned, co-pending application filed on Dec. 29, 2006, entitled "Diagnostic Test For The Detection Of A Molecule Or Drug In Whole Blood" in the name(s) of Frank C. Grenier, Ryan F. Workman, Hina N. Syed, and Ali Salman U.S. Ser. No. 60/882,732 is explicitly incorporated by reference in its entirely.

The commonly owned, co-pending application filed on Dec. 29, 2006, entitled "Non-Denaturing Lysis Reagent For Use With Capture-In-Solution Immunoassay" in the name(s) of Shelley Holets-McCormack U.S. Ser. No. 60/878,017 is explicitly incorporated by reference in its entirely.

The commonly owned, co-pending application filed on Dec. 29, 2006, entitled "Improved Assay For Immunosuppressant Drugs" in the name(s) of Susan Drengler, and Wade Baugher U.S. Ser. No. 60/882,863 is explicitly incorporated by reference in its entirely.

In addition, all other publications, patents, and patent applications cited herein are hereby incorporated by reference in their entirety for all purposes.

EXAMPLES

The following examples are offered to illustrate, but not to limit, the claimed invention.

Example 1

Lysis and Immunoassay of a Blood Sample for Sirolimus

This example illustrates the use of a non-denaturing lysis reagent to lyse a blood sample and carry out an automated immunoassay for sirolimus.

A lysis reagent is prepared by mixing propylene glycol and ethanol at a volume:volume ratio of 4:1. Lysis of a blood sample is accomplished by mixing 100 μL of sample with 200 μL of lysis reagent by vortexing vigorously for 5-10 seconds. Lysis is complete in less than 1 min at room temperature. The resulting lysis mixture is assayed on an automated ARCHITECT i2000 analyzer (Abbott Laboratories, Abbott Park, Ill.) by:

(1) Mixing 10-40 uL of the lysis mixture with 50 uL of microparticles coated with goat anti-mouse antibody (from Sigma, St. Louis, Mo.) and mouse anti-sirolimus antibody (prepared as described below).
(2) Incubating the assay mixture for approximately 18 minutes at 33-38 degrees C. The sirolimus in the sample binds the anti-sirolimus antibody on the microparticles.
(3) Adding 20 uL of acridinium-sirolimus conjugate to the reaction mixture.
(4) Incubating the reaction mixture for approximately 4 minutes at 33-38 degrees C. The acridinium-sirolimus conjugate binds free anti-sirolimus binding sites.
(5) Washing the microparticles with a phosphate buffer.
(6) Adding Pre-trigger (acid solution) and Trigger (basic solution) to cause the captured acridinium-sirolimus label to emit light, which is measured by the instrument.

The sirolimus binding antibody was produced as follows: Female RBf/Dnj mice were administered 3 monthly boosts of a sirolimus-27-CMO-tetanus toxoid immunogen, followed by an immunization with sirolimus-42-HS-tetanus toxoid preparation on the 4th month. Seven months later, an intrasplenic pre-fusion boost was administered to the animals using the sirolimus-27-CMO-tetanus toxoid immunogen 3 days prior to the fusion. Splenic B-cells were isolated and used in a standard PEG fusion with the SP2/0 myeloma. Confluent cultures were screened for anti-sirolimus activity 10-14 days later in a microtiter EIA, and positive cultures were cloned using limiting dilution cloning technique. Isolated clones were scaled up in IMDM w/FBS (Invitrogen) tissue culture medium, and secreted antibody was affinity purified using Protein A.

What is claimed is:

1. A method for preparing a test sample for use in an assay for an analyte that is a non-protein molecule, the method comprising contacting the test sample with a lysis reagent to form a lysis mixture, wherein the analyte, if present in the sample, is released from a cell or other component within the sample, the lysis reagent comprising a glycol selected from the group consisting of ethylene glycol, propylene glycol, and an analog thereof; wherein:

at least one alcohol having five or fewer carbons is included in the lysis reagent or added to the lysis mixture, the ratio of glycol to alcohol is in the range of about 4:1 to about 1:4, and, after addition of the alcohol, the lysis mixture is a homogeneous mixture that is sufficiently free of large particulates to allow automated pipetting of the mixture;

the method does not comprise contacting the test sample or the lysis mixture with a detergent;

the lysis mixture does not comprise a chelating agent; and the lysis mixture can be assayed without the need for a separation step.

2. The method of claim 1, wherein the alcohol is included in the lysis reagent.

3. The method of claim 1, wherein the test sample comprises a human blood sample.

4. The method of claim 1, wherein the alcohol is selected from the group consisting of methanol, ethanol, and propanol.

5. The method of claim 2, wherein the ratio of glycol to alcohol is in the range of about 4:1 to about 1:2.

6. The method of claim 2, wherein the test sample is added to the lysis reagent at a ratio in the range of about 2:1 to about 1:2.

7. The method of claim 1, wherein the method does not comprise centrifuging the lysis mixture.

8. The method of claim 1, wherein the assay detects an analyte that is bound to one or more binding proteins in the test sample, the method additionally comprising contacting the test sample or the lysis mixture with an agent that releases the analyte from said one or more binding proteins.

9. The method of claim 8, wherein the agent competes with the analyte for binding to said one or more binding proteins.

10. The method of claim 9, wherein the analyte comprises an immunosuppressant drug, and the agent comprises a different, but structurally similar, immunosuppressant drug.

11. The method of claim 8, wherein the agent comprises a protease that degrades said one or more binding proteins.

12. A lysis reagent mixture comprising:

a test sample that comprises an analyte that is a non-protein molecule;

a glycol selected from the group consisting of ethylene glycol, propylene glycol, and an analog thereof; and at least one alcohol having five or fewer carbons, wherein the ratio of glycol to alcohol is in the range of about 4:1 to about 1:4; wherein:

the analyte, if present in the sample, is released from a cell or other component within the sample;

the lysis reagent mixture is a homogeneous mixture that is sufficiently free of large particulates to allow automated pipetting of the mixture; and the lysis reagent mixture does not comprise a detergent and can be assayed without the need for a separation step.

13. The lysis reagent mixture of claim 12, wherein the test sample comprises a human blood sample.

14. The lysis reagent mixture of claim 12, wherein the alcohol is selected from the group consisting of methanol, ethanol, and propanol.

15. The lysis reagent mixture of claim 12, wherein the ratio of glycol to alcohol is in the range of about 4:1 to about 1:2.

16. A method for assessing the presence or concentration of an analyte that is a non-protein molecule in a whole blood sample, the method comprising:

contacting the whole blood sample with a lysis reagent to form a lysis mixture, the lysis reagent comprising a glycol selected from the group consisting of ethylene glycol, propylene glycol, and an analog thereof, wherein at least one alcohol having five or fewer carbons is included in the lysis reagent or added to the lysis mixture at a glycol to alcohol ratio in the range of about 4:1 to about 1:4, and, after addition of the alcohol, the lysis mixture is a homogeneous mixture that is sufficiently free of large particulates to allow automated pipetting of the mixture, and the lysis mixture does not comprise a detergent or a chelating agent, wherein the analyte, if present in the sample, is released from a cell or other component within the sample; and assaying the lysis mixture for the analyte without any separation step.

17. The method of claim 16, wherein the alcohol is included in the lysis reagent.

18. The method of claim 16, wherein the assay comprises an immunoassay.

19. The method of claim 16, wherein the analyte comprises an immunosuppressant drug.

20. The method of claim 19, wherein the immunosuppressant drug is selected from the group consisting of sirolimus, tacrolimus, everolimus, temsorolimus, zotarolimus, cyclosporine, and analogs of any of these compounds.

21. The method of claim 16, wherein the test sample comprises a human blood sample.

22. The method of claim 16, wherein the alcohol is selected from the group consisting of methanol, ethanol, and propanol.

23. The method of claim 16, wherein the ratio of glycol to alcohol is in the range of about 4:1 to about 1:2.

24. The method of claim 16, wherein the test sample is added to the lysis reagent at a ratio in the range of about 2:1 to about 1:2.

25. The method of claim 16, wherein the method does not comprise centrifuging the lysis mixture.

26. The method of claim 16, wherein the assay detects an analyte that is bound to one or more binding proteins in the test sample, the method additionally comprising contacting the test sample or the lysis mixture with an agent that releases the analyte from said one or more binding proteins.

27. The method of claim 26, wherein the agent competes with the analyte for binding to said one or more binding proteins.

28. The method of claim 26, wherein the analyte is an immunosuppressant drug and the agent comprises a different, but structurally similar, immunosuppressant drug.

29. The method of claim 26, wherein the agent comprises a protease that degrades said one or more binding proteins.

30. A method for preparing a test sample for use in an assay for an analyte that is a non-protein molecule, the method comprising contacting the test sample with a lysis reagent to form a lysis mixture, wherein the analyte, if present in the sample, is released from a cell or other component within the sample, the lysis reagent comprising a glycol selected from the group consisting of ethylene glycol, propylene glycol, and an analog thereof; wherein:

at least one alcohol having five or fewer carbons is included in the lysis reagent or added to the lysis mixture, and the ratio of glycol to alcohol in the range of about 5:1 to about 1:5, and, after addition of the alcohol, the lysis mixture is a homogeneous mixture that is sufficiently free of large particulates to allow automated pipetting of the mixture;

the method does not comprise contacting the test sample or the lysis mixture with a detergent;

the lysis mixture does not comprise a chelating agent; and
the lysis mixture can be assayed without the need for a separation step.

31. A lysis reagent mixture comprising:
a test sample that comprises an analyte that is a non-protein molecule;
a glycol selected from the group consisting of ethylene glycol, propylene glycol, and an analog thereof; and
at least one alcohol having five or fewer carbons, wherein the ratio of glycol to alcohol is in the range of about 5:1 to about 1:5; wherein:
the analyte, if present in the sample, is released from a cell or other component within the sample;
the lysis reagent mixture is a homogeneous mixture that is sufficiently free of large particulates to allow automated pipetting of the mixture; and
the lysis reagent mixture does not comprise a detergent or a chelating agent and can be assayed without the need for a separation step.

32. A method for assessing the presence or concentration of an analyte that is a non-protein molecule in a whole blood sample, the method comprising:
contacting the whole blood sample with a lysis reagent to form a lysis mixture, the lysis reagent comprising a glycol selected from the group consisting of ethylene glycol, propylene glycol, and an analog thereof, wherein at least one alcohol having five or fewer carbons is included in the lysis reagent or added to the lysis mixture at a glycol to alcohol ratio in the range of about 5:1 to about 1:5, and, after addition of the alcohol, the lysis mixture is a homogeneous mixture that is sufficiently free of large particulates to allow automated pipetting of the mixture, and the lysis mixture does not comprise a detergent or a chelating agent, wherein the analyte, if present in the sample, is released from a cell or other component within the sample; and
assaying the lysis mixture for the analyte without any separation step.

33. The method of any of claims 1, 16, 30, and 32, wherein the glycol is selected from the group consisting of ethylene glycol and propylene glycol.

34. The lysis reagent mixture of claim 12 or 31, wherein the glycol is selected from the group consisting of ethylene glycol and propylene glycol.

35. A method for preparing a test sample for use in an assay for an analyte that is a non-protein molecule the method comprising contacting the test sample with a lysis reagent to form a lysis mixture, wherein the analyte, if present in the sample, is released from a cell or other component within the sample, the lysis reagent consisting of a glycol selected from the group consisting of ethylene glycol, propylene glycol, and an analog thereof and at least one alcohol having five or fewer carbons, wherein the ratio of glycol to alcohol is in the range of about 4:1 to about 1:4, and, after addition of the alcohol, the lysis mixture is a homogeneous mixture that is sufficiently free of large particulates to allow automated pipetting of the mixture;
wherein the method does not comprise contacting the test sample or the lysis mixture with a detergent; and
the lysis mixture can be assayed without the need for a separation step.

36. A method for preparing a test sample for use in an assay for an analyte that is a non-protein molecule, the method comprising contacting the test sample with a lysis reagent to form a lysis mixture, wherein the analyte, if present in the sample, is released from a cell or other component within the sample, the lysis reagent comprising a protease that degrades one or binding proteins that bind the analyte, a glycol selected from the group consisting of ethylene glycol, propylene glycol, and an analog thereof; and
at least one alcohol having five or fewer carbons is included in the lysis reagent or added to the lysis mixture, the ratio of glycol to alcohol is in the range of about 4:1 to about 1:4, and, after addition of the alcohol, the lysis mixture is a homogeneous mixture that is sufficiently free of large particulates to allow automated pipetting of the mixture;
the method does not comprise contacting the test sample or the lysis mixture with a detergent; and
the lysis mixture can be assayed without the need for a separation step.

37. A method for assessing the presence or concentration of an analyte that is a non-protein molecule in a whole blood sample, the method comprising:
contacting the whole blood sample with a lysis reagent to form a lysis mixture, the lysis reagent comprising a protease that degrades one or binding proteins that bind the analyte, a glycol selected from the group consisting of ethylene glycol, propylene glycol, and an analog thereof, wherein at least one alcohol having five or fewer carbons is included in the lysis reagent or added to the lysis mixture at a glycol to alcohol ratio in the range of about 4:1 to about 1:4, and, after addition of the alcohol, the lysis mixture is a homogeneous mixture that is sufficiently free of large particulates to allow automated pipetting of the mixture, and the lysis mixture does not comprise a detergent, wherein the analyte, if present in the sample, is released from a cell or other component within the sample; and
assaying the lysis mixture for the analyte without any separation step.

* * * * *